United States Patent [19]

Brush

[11] Patent Number: 5,420,330
[45] Date of Patent: May 30, 1995

[54] LIPO-PHOSPHORAMIDITES

[75] Inventor: Charles K. Brush, Whitefish Bay, Wis.

[73] Assignee: Pharmacia P-L Biochemicals Inc., Milwaukee, Wis.

[21] Appl. No.: 578,377

[22] Filed: Sep. 7, 1990

[51] Int. Cl.⁶ .................................................. C07F 9/24
[52] U.S. Cl. ..................................... 558/185; 558/157; 558/169; 558/168; 558/180; 552/104; 536/25.3; 536/25.34
[58] Field of Search ............................ 536/29, 27, 28; 558/169, 180, 168, 157, 185; 560/222, 223, 224; 552/104

[56] References Cited

U.S. PATENT DOCUMENTS 4,914,210  4/1990  Levinson et al. .................... 558/169

FOREIGN PATENT DOCUMENTS

WO8809810 12/1988 WIPO .
8903891  5/1989 WIPO .................................. 536/29

OTHER PUBLICATIONS

Letsinger et al. Proc. Natl. Acad. Sci. USA, vol. 86, pp. 6553–6556, Sep. 1989.
S. Horvath et al., 154 Meth. In Enzym. 314–326 (1987).
J. Coull et al., 27 Tetr. Let. 3991–3994 (1986).
R. Shea et al., 18 Nuc. Acids Res. 3777–3783 (1990).
A. Kabanov et al., 259 Febs Let. 327–330 (1990).
F. Eckstein, 54 Ann. Rev. Biochem. 367–402 (1985).
B. Uznanski et al., 26 Chem. Scripta 221–224 (1985).
P. Miller et al., 25 Biochem. 5092–5097 (1986).
E. Stirchak et al., 52 J. Org. Chem. 4202–4206 (1987).
J. Haralambidis et al., 28 Tetr. Let. 5199–5202 (1987).
R. Letsinger et al., 110 J. Am. Chem. Soc. 4470–4471 (1988).
F. Seela et al., 71 Hel. Chem. Acta 1813–1823 (1988).
J. Habener et al., 85 P.N.A.S. 1735–1739 (1988).
M. Urdea et al., 16 Nucl. Acids Res. 4937–4956 (1988).

Primary Examiner—Douglas W. Robinson
Assistant Examiner—James D. Wilson
Attorney, Agent, or Firm—Quarles & Brady

[57] ABSTRACT

Ether variant lipids bound to phosphoramidites are disclosed. These can be used to create oligonucleotides that are linked to stable lipid-like units. For example, dialkyl glycerols are linked to phosphoramidites.

4 Claims, 4 Drawing Sheets

LIPO-PHOSPHORAMIDITES

TECHNICAL FIELD

This invention relates generally to compounds that can be linked to oligonucleotides so as to thereby render the oligonucleotides more hydrophobic. More particularly, it relates to ether variants of lipids that are linked to phosphoramidites.

BACKGROUND ART

Automated DNA synthesizers have made the production of oligodeoxynucleotides a routine laboratory exercise (S. Horvath et al., 154 Methods in Enzymology 314–326 (1987)). The disclosure of this article and of all other articles recited herein are incorporated by reference as if fully set forth herein. Researchers have now turned their attention to the modification of oligonucleotides.

Nucleosides with different substituents on the bases have been used to prepare modified oligonucleotides. See generally F. Seela et al., 71 Helv. Chim. Acta 1813 (1988); J. Haebner et al., 85 P.N.A.S.U.S.A. 1735 (1988). As such, linkers have been developed for the conjugation of oligonucleotides to solid supports, peptides (J. Haralambidis et al., 28 Tet. Let. 5199 (1987)), reporter labels, (M. Urdea et al., 16 J. Nuc. Acids Res. 4937 (1988)) and biotin. Replacement of the internucleotide phosphodiester linkage with phosphorothioate (F. Eckstein, 54 Ann. Rev. Biochem. 367 (1985)), methylphosphonate (P. Miller et al., 25 Biochemistry 5092 (1986)), carbamate (E. Stirchak et al., 52 J. Org. Chem. 4202 (1987)), alkyl phosphotriester (B. Uznanski et al., 26 Chemica Scripta 221 (1986)), or cationic alkylphosphoramidate (R. Letsinger et al., 110 J. Am. Chem. Soc. 4470 (1988)) linkages have been reported.

Attempts to attach oligonucleotides to certain long chain moieties have been reported. See H. Tullis PCT 88-368625/09810 (1988); A. Kabanov et al., 259 FEBS Let. 327 (1990) (article itself not prior art) and R. Letsinger et al., 86 P.N.A.S. USA 6553 (1989). However, the need still exists for a way to more easily link hydrophobic moieties to a wide variety of oligonucleotides. Such compounds are needed to improve and/or modify membrane permeability, nuclease resistance, binding, protein and complementary DNA and RNA isolation techniques, and solubility.

DISCLOSURE OF INVENTION

In one aspect, the invention provides a compound having the following moiety:

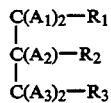

wherein $A_1$, $A_2$ and $A_3$ are selected from the group of $CH_3$ and H, and $R_1$, $R_2$ and $R_3$ are selected from the group of OH, O-alkenyl, O-alkyl, O-aryl, O-aralkyl, O-oligonucleotide, O-fluorescent label containing moiety, and other organic ether moieties; at least one of $R_1$, $R_2$, and $R_3$ is O-oligonucleotide; and at least one of $R_1$, $R_2$, and $R_3$ is selected from the group of O-alkenyl (with 12–22 carbons in the O-alkenyl), O-alkyl (with 12–22 carbons in the alkyl), O-aryl (with 6–22 carbons in the O-aryl), and O-aralkyl (with 7–22 carbons in the O-aralkyl). The term "oligonucleotide" is meant to include moieties that contain a nucleotide chain of one or more nucleoside residues (either DNA or RNA), with or without all or part of a phosphate or other linking group present on the termini of the chain, and regardless of whether or not in the salt or charged forms. The oligonucleotide chain can be linked to the lipid moiety at either its 3' or 5' end.

In another aspect, the invention provides a compound having the following moiety:

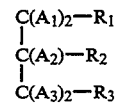

wherein $A_1$, $A_2$ and $A_3$ are selected from the group of $CH_3$ and H, and $R_1$, $R_2$, and $R_3$ are selected from the group of O-alkenyl, O-alkyl, O-aryl, O-aralkyl, O-phosphoramidite and other organic ether moieties; at least one of $R_1$, $R_2$ and $R_3$ is O-phosphoramidite; at least one of $R_1$, $R_2$, and $R_3$ is selected from O-alkenyl (with 12–22 carbons in the alkenyl) and O-alkyl (with 12–22 carbons in the alkyl), O-aryl (with 6–22 carbons in the O-aryl) and O-aralkyl (with 7–22 carbons on the O-aralkyl). Preferably the alkyl and alkenyl groups are of the n-alkyl or n-alkenyl type.

A preferred other "organic ether moiety" is 4', 4'-dimethoxytrityl ("DMTr"), and DMTr is preferably at the $R_3$ position if present. This and certain other ether groups are excellent protecting groups. Note that the term "organic ether moiety" is being used here and in the claims to indicate a bridging oxygen bound to a carbon, with that carbon having no other oxygens, and that bridging oxygen is bound to the rest of the claimed structure.

Also disclosed is a method for producing the claimed lipo-oligonucleotides. The method uses the claimed lipo-phosphoramidites to couple to an oligonucleotide.

Lipid variants that use ether (as distinguished from ester) bonds to attach the lipid structure provide a securely attached set of fatty acid-like moieties that provide certain hydrophobic characteristics while being resistant to compounds used in deprotection. The phosphoramidite provides a means to link the lipo unit to oligonucleotide moieties. The lipo-phosphoramidites can be sold as reagents which can be readily used with commercially available phosphoramidite-based synthesizer systems to synthesize the claimed lipo-oligonucleotides. They may also have other uses (e.g. probes, purifying agents).

The objects of the invention therefore include providing compounds of the above kind:

(a) which have modified membrane permeability;
(b) which have modified solubility;
(c) which are synthesized efficiently and at relatively low cost;
(d) which have deprotection resistant ether bonds on at least part of the lipid portion; and
(e) which can readily be attached to fluorescent labels.

These and still other objects and advantages of the present invention will be apparent from the description below. However, this description is only of the preferred embodiments. The claims should therefore be looked to in order to assess the full scope of the invention.

BEST MODES FOR CARRYING OUT THE INVENTION

A. Overview

Figure 1:
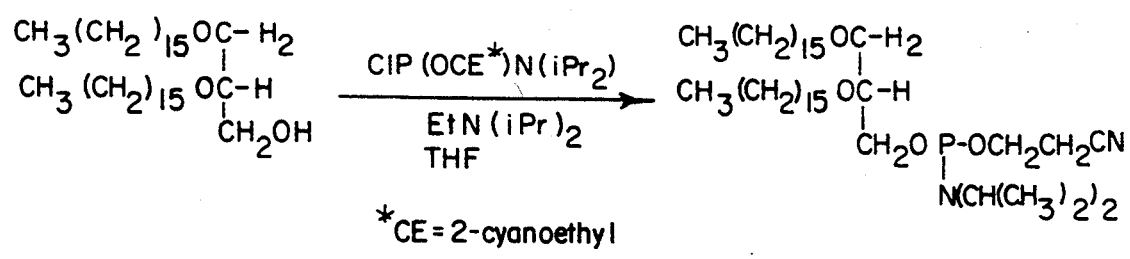
FIG. 1 shows a schematic of a synthesis of a lipo-oligonucleotide through the intermediates of a lipo-phosphoramidite and a protected lipo-oligonucleotide.
Figure 1:
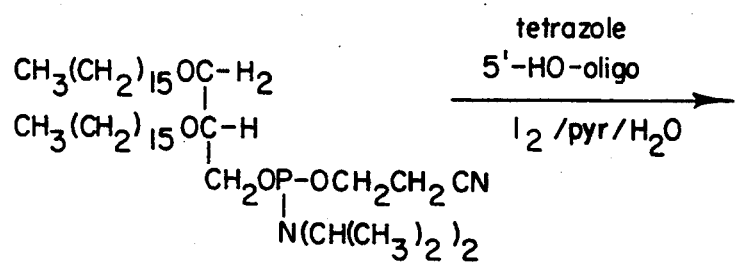
Figure 1:
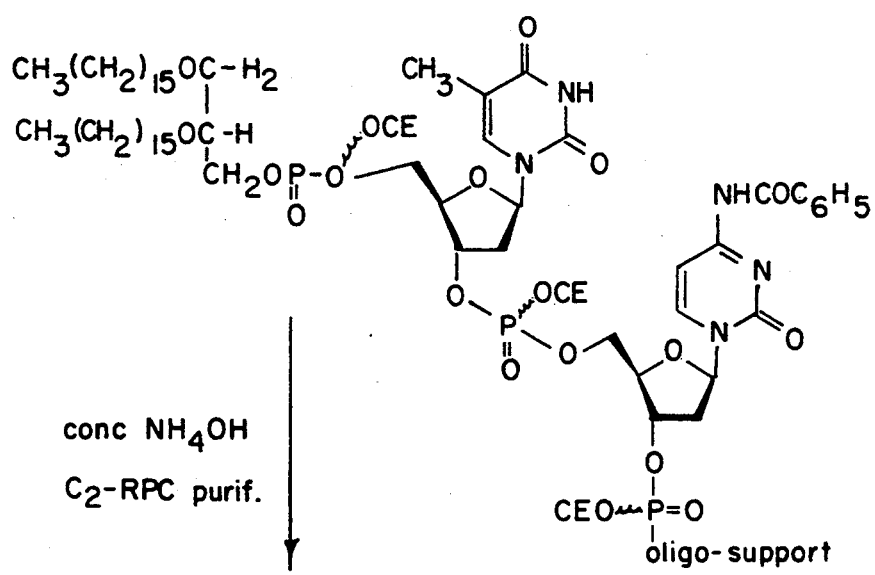
Figure 1:
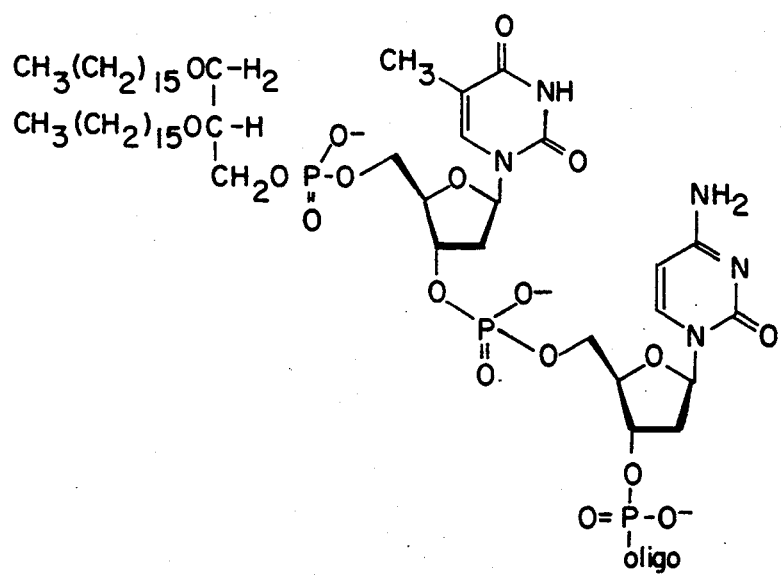

Alkyl or alkenyl glycerols are the preferred starting materials for the synthesis of lipo-oligonucleotides and lipo-phosphoramidites. Alkyl or alkenyl glycerols can be purchased or can be synthesized using conventional techniques. For example, dialkyl glycerols can be made from glycerol and alkyl tosylates. In accordance with the present invention, an amidite group is then added to the glycerol to form lipo-phosphoramidites. If synthesis of a lipo-oligonucleotide is desired, a coupling reaction in a oligonucleotide synthesizer can connect the lipo-phosphoramidite to the end of an oligonucleotide chain.

If a fluorescent residue is to be attached to the lipid group, the synthesis is begun with a structure that has an OH group in two positions, such as batyl alcohol. An ether protecting group, such as DMTr, is added to one position. A lipo-phosphoramidite is created by addition of an amidite group to the other position. After addition of the amidite group, a coupling reaction in a synthesizer connects the lipo-phosphoramidite to an end of the oligonucleotide. Deprotection can then take place. The fluorescent label is then added to the first position. In an example, an aminolinker is first added to the $R_1$ position on the synthesizer. After deprotection, a fluorescein type moiety is connected to this aminolinker group.

B. Preparation Of A Lipo-Phosphoramidite 1,2-di-O-hexadecyl-rac-glycerol (Sigma, 0.125 g, 0.00023 mol) (a compound with $R_1$ and $R_2$ as the 16 carbon alkyl ethers and an OH at $R_3$) was dried by co-evaporation with dry (molecular sieves) toluene twice and dry (molecular sieves) THF twice. The solid residue was dissolved in 2 ml of dry THF under dry nitrogen and cooled to 0° C. in an ice bath. Some of the material crystallized from the cold THF.

The next step is linking a phosphoramidite at the $R_3$ position. Diisopropylethylamine (80 μl, 0.0046 mol) was added to the THF solution dropwise, followed by 55 μl of β-cyanoethyl-N,N-diisopropylaminophosphochloridite (0.00023 mol). This technique is generally adaptable to modify glycerols with an OH group to a phosphoramidite where the other groups are long chain ethers or ether-protecting groups such as DMTr.

The reaction was removed from the ice bath and allowed to warm to room temperature. The crystallized dialkylglycerol dissolved slowly and diisopropylethylamine hydrochloride precipitated.

The reaction mixture was stirred for 45 minutes at room temperature and then diluted with 10 ml of dichloromethane and extracted with 5 ml of cold 0.5 M sodium bicarbonate, pH 9.4. The organic layer was dried with anhydrous sodium sulfate and evaporated to leave a clear colorless syrup. A vacuum pump was used to remove the last traces of solvent and diisopropylethylamine.

C. Preparation Of A Lipo-Oligonucleotide

The crude 1,2-di-O-hexadecyl-rac-glyceryl-β-cyanoethyl-N, N-diisopropylphosphoramidite was dissolved in 2 ml of dry THF to give a ≈0.085 M solution. Using the lipo-phosphoramidite as the last "unit," an 11mer (oligonucleotide with eleven residues) linked to the lipo unit was prepared on a 10 μmol scale, using a commercially available Pharmacia Gene Assembler Plus[R] automated synthesizer in the method described below. Automated synthesis in general terms is discussed in S. Horvath et al., 154 Meth. Enzym. 314–326 (1987).

In this regard, the Gene Assembler Plus uses phosphite triester chemistry. The hydroxyl group at the phosphorous atom in each base unit is protected using a β-cyanoethyl group. The phosphorous atom also bears a N,N-diisopropyl group as reaction site in the coupling reaction. The β-cyanoethyl group is removed by treatment with concentrated ammonia. This means that both the base protecting groups and the β-cyanoethyl group can be removed in one step using ammonia.

A fully protected nucleotide is referred to as an amidite in this technique. The 5' OH is protected by DMTr and the 3' phosphorus is in amidite form. To synthesize oligonucleotides, one needs to have previously obtained deoxyadenasine, deoxycytidine, deoxyguanasine and thymidine amidite versions.

A polystyrene or controlled pore glass support is the starting point for the synthesis. The first nucleoside is linked to the solid phase by known techniques (e.g. with a spacer). The reaction cycle preferably consists of the following steps:

(a) Ethylene dichloride (EDC) wash of the support;

(b) Deprotection of the 5'-hydroxyl group of the terminal 2-deoxyribose unit, removing the DMTr group (using dichloro- or trichloroacetic acid);

(c) EDC wash, removing the DMTr group and acid;

(d) Acetonitrile wash to obtain waterfree conditions for the coupling;

(e) Forming a 3'–5' internucleotide linkage with the phosphorous-containing group of an incoming protected deoxyribonucleotide catalyzed by tetrazole in a coupling step;

(f) Acetonitrile wash removing tetrazole and unreacted amidites (nucleotides);

(g) Capping of unreacted 5'-hydroxyl groups as acetates using $Ac_2O$ and 4-dimethylaminopyridine and 2, 4, 6-collidine in acetonitrile;

(h) Oxidation of the phosphite triester bridge using iodine, collidine and water in acetonitrile; and (i) Acetonitrile wash removing the yellow oxidation solution.

The process (a-i) is repeated until the desired oligonucleotide sequence has been produced.

To create the lipo-oligonucleotide, these coupling conditions were used except that the lipo-phosphoramidite was substituted as the last "unit", and the coupling time was extended to seven minutes for the lipo unit. To obtain the final product, we deprotected with $NH_3$, cleaved the oligonucleotide from the support, and purified with preparative reverse-phase FPLC (ProRPC 5/10, 20–100% acetonitrile/triethylammonium acetate, pH 7, 20 minute gradient, 2 ml/minute; retention time, 8.4 minutes). The non-lipo-oligonucleotide eluted at 1.15 minutes.

Experimental evidence accumulated thus far for the lipo-11-mer, in which the lipo-alkyl groups are hexadecyl, indicates that the lipo-oligonucleotide has a much greater affinity for reverse phase supports than the corresponding non-lipo-oligonucleotide. $^1$H NMR studies in aqueous solution suggest considerable aggregation of the lipo-oligonucleotide, which persists (to a much lesser extent) at 65° C., far above the temperature at which the non-lipo-oligonucleotide becomes completely denatured to a random coil conformation.

It will be appreciated that the above technique should be useful for synthesizing a wide range of lipo-oligonucleotides. The $R_1$, $R_2$, or $R_3$ may be O-alkenyl chains, O-alkyl chains, or OH. An oligonucleotide is added to at least one of the three positions. The oligonucleotide may be in a charged form or complexed as a salt. Where one of $R_1$, $R_2$, or $R_3$ is a hydroxyl-protecting group like DMTr, that site can in turn provide a point for further linkages (e.g. fluorescent labels, other nucleotides).

D. Preparation of A Sandwiched Lipo-Oligonucleotide.

Figure 2:
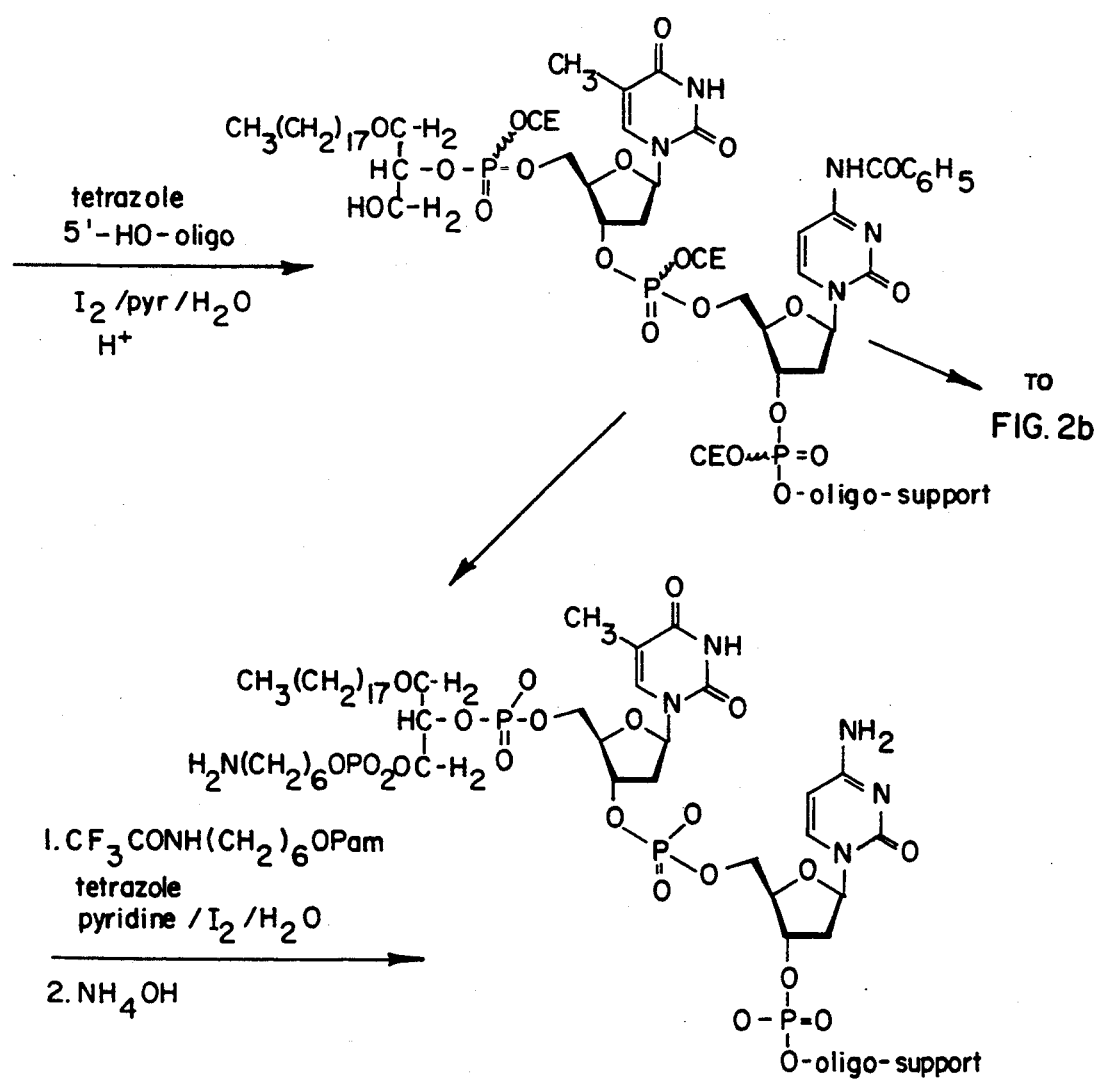
FIG. 2 shows schematic syntheses of two other preferred embodiments.

The synthesis of a preferred embodiment where a lipo unit is in the interior of a compound is shown in FIG. 2. First, one prepares a lipo unit with two alcohols. One is protected with a DMTR, the other is linked to the amidite. After creating the lipo-oligonucleotide, the DMTR is removed and the remaining OH linked to a fluorescent label as in FIG. 2a (or if desired another oligonucleotide as in FIG. 2b). In one experiment (see FIG. 2) DL-Batyl alcohol (1-0-octadecyl-rac-glycerol, Sigma, 6.23 g 0.0181 mol) was dried by co-evaporation twice with dry pyridine. It was redissolved in 100 ml of dry pyridine and cooled to 5° C. in an ice bath. Dimethoxytrityl chloride (6.77 g, 0.02 mol) was added in small portions, the ice bath removed, and the reaction stirred overnight.

The pyridine was evaporated and the residue partitioned between dichloromethane and water. The organic layer was extracted with aqueous sodium bicarbonate, dried with anhydrous sodium sulfate, and evaporated. The product was purified by chromatography on silica gel with dichloromethane/hexane/triethylamine (77:20:3) as the eluant. The product, dimethoxytrityl-batyl alcohol, (1-0-(4,4'-dimethoxytrityl)-2-0-octadecyl-rac-glycerol, 9.3 g, 79% yield) was characterized by $^1$H NMR spectroscopy and TLC and estimated to be >95% pure, the balance probably being dimethoxytrityl alcohol.

The phosphoramidite of dimethoxytrityl-batyl alcohol (see FIG. 2) was then prepared. Diisopropyl ethylamine (4.88ml, 0.00145 mol) was added dropwise to 4.54g (0,007 mol) of dimetroxytrityl-batyl alcohol. 2.88 mL (0,007 mol) of β-cyanoethyl-N,N-diisopropylaminophosphochloridite was then added. The reaction was warmed to room temperature. After 45 minutes of stirring, the mixture was diluted with 10 ml dichloromethane and extracted with 5 ml cold 0.5M sodium bicarbonate, pH 9.4. The product was chromatographed on silica gel with hexanes/ether/triethylamine (79.75:20:0.25) as the eluant. (The product (3.85 g, 65%) was characterized by $^1$H NMR and TLC and estimated to be >97% pure). The dimethoxytrityl-batyl alcohol phosphoramidite was then used on a Gene Assembler Plus as described above for the dihexadecylglyceryl phosphoramidite.

Figure 2A:
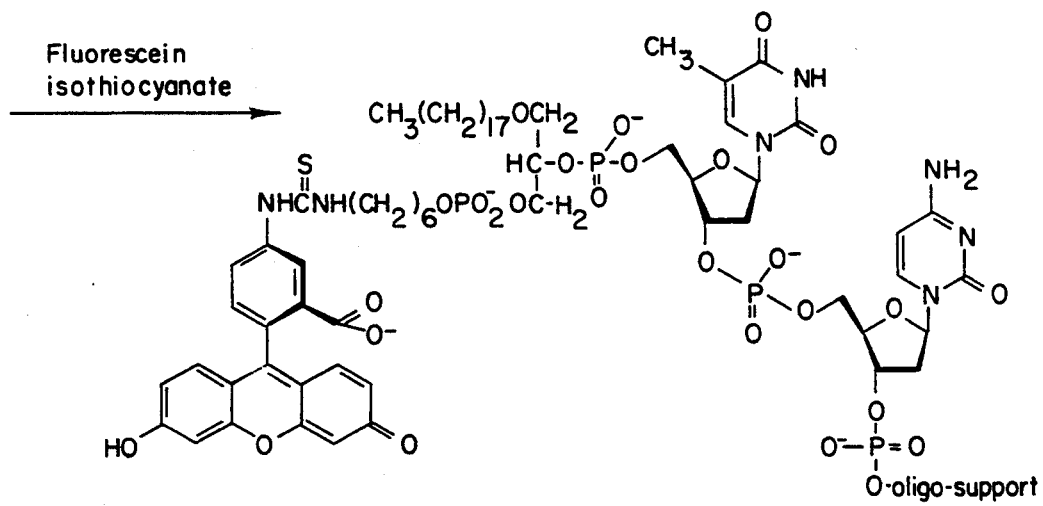
FIG. 2(a) shows a schematic synthesis where the compound is linked to a fluorescent label.
Figure 2B:
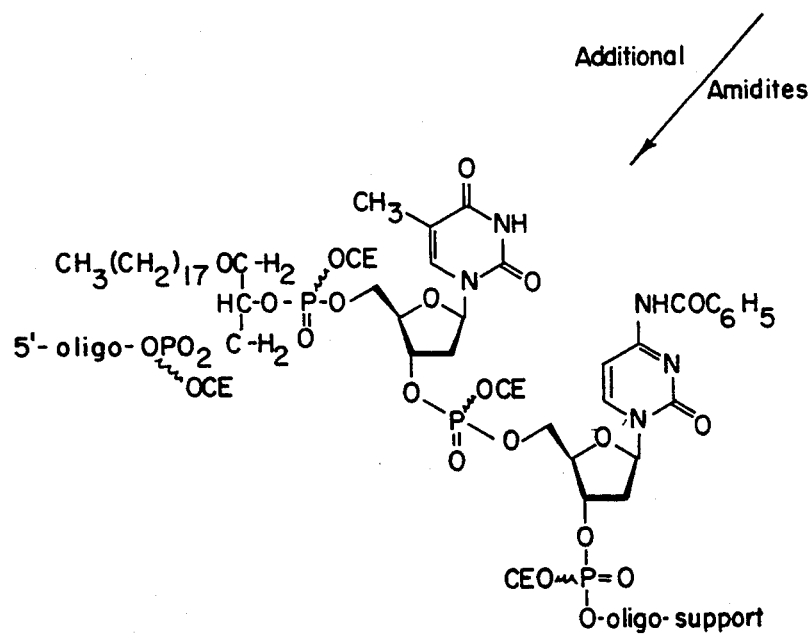
FIG. 2(b) shows a schematic synthesis where the compound is linked to a second oligonucleotide.

Since the batyl amidite is protected by a dimethoxytrityl group, it is possible to detritylate it and couple additional nucleoside phosphoramidites to it at that position (FIG. 2b). One ends up with lipo units in the middle of a nucleotide chain. The lipo-oligonucleotides (15mers) were purified and characterized as described above, using ProRPC FPLC$^R$ chromatography, (20–60% acetonitrile/0.1 M triethylammonium acetate, pH 7, 20 min, 2 ml/min). Retention times for the different reaction products were:

| | |
|---|---|
| 5'-end batyl-15 mer: | 4–7 min (broad) |
| 2nd from 3'-end batyl-15 mer: | 4–8 min (broad) |
| 5', 2nd from 3'-end di-batyl-15 mer: | 9–12 min (broad) |
| middle batyl-15 mer: | 3–6 min (broad) |

Instead of adding another oligonucleotide, a marker moiety can be added. As shown in FIG. 2a, after DMTR deprotection, an aminolinker can be added to a batyl group at the $R_2$ position by standard methods. We chose to couple a fluorescein moiety to the lipo-oligonucleotide via an isothiocyanate derivative. See J. Coull et al, 27 Lett. 3991 (1986); M. Urdea et al, 16 Nuc. Acids Res. 4937 (1988). The resulting fluorescein-batyl-oligonucleotide showed the expected spectral and FPLC characteristics (retention time using the system described above was 6–9 min (broad)).

The product was tested as a primer using routine conditions on an A.L.F. Automated Laser DNA Sequencer (Pharmacia LKB) and found to produce a readable sequence. Although fluorescein was the fluorescent label employed in this reaction, other fluorescent labels can be linked to the deprotected OH on the lipo unit. Also, the particular linker to the label ($NH(CH_2)_6OPO_2O$) could be varied.

E. Preparation of a Lipo-3'-Oligonucleotide.

Figure 3:
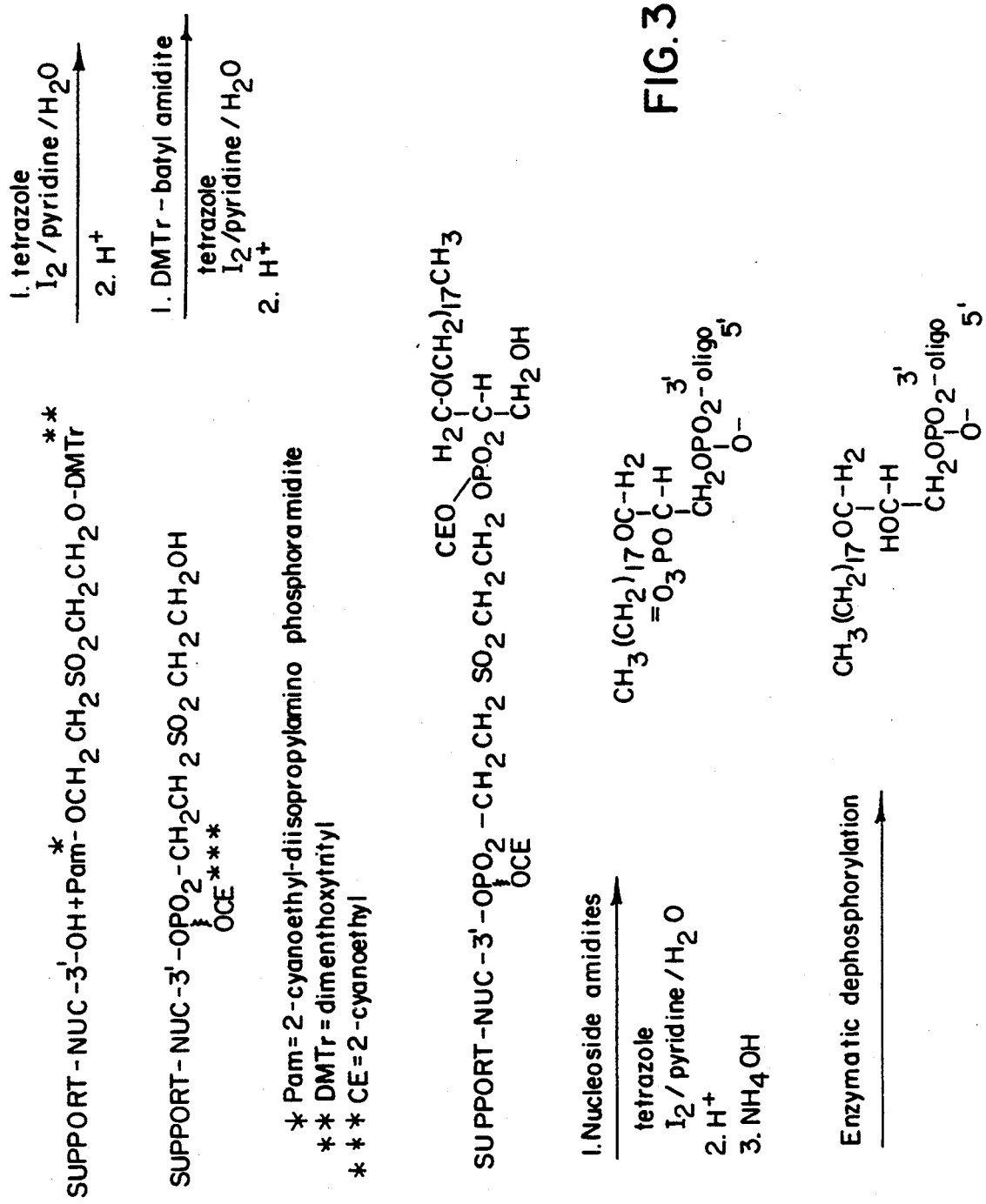
FIG. 3 shows a schematic of the synthesis of an embodiment in which the lipid moiety is attached at the 3' terminus of the oligonucleotide.

In some instances, it may be advantageous to have the 5' terminus of an oligonucleotide chain available for further reactions. In these situations, the 3' terminus of the oligonucleotide can be attached to the lipo-oligonucleotide. The batyl group may be introduced at the second position from the 3'-end of an oligonucleotide by the use of a standard nucleoside support and addition of the batyl amidite as the first cycle. As shown in FIG. 3, it is possible to have the batyl group at the ultimate 3' position by the following procedure:

1. Start with a standard nucleoside support.
2. Add a "chemical phosphorylating amidite" (see FIG. 3) as the first cycle.

Add the batyl amidite as the second cycle.

Continue with the addition of ordinary nucleoside amidites.

5. Deprotect with ammonia, as usual; the "chemical phosphorylating linkage" decomposes to leave the batyl phosphate at the 3'-end.

6. Treatment with a dephosphorylating enzyme, such as polynucleotide kinase or calf alkaline phosphatse, should remove the 3'-phosphate to give the desired 3'-batyl oligonucleotide.

Thus, it can be seen that the present invention provides general techniques to couple lipo units to oligonucleotides. The preferred embodiments are merely examples of these techniques. The claims should therefore be looked to in order to assess the full scope of the claims.

I claim:

1. A compound having the following structure:

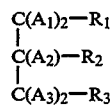

wherein $A_1$, $A_2$ and $A_3$ are selected from the group consisting of $CH_3$ and H, and $R_1$, $R_2$ and $R_3$ are selected from the group consisting of O-alkyl with 16–18 carbons an O-trityl moiety, and O-phosphoramidite;

at least one of $R_1$, $R_2$ and $R_3$ is O-phosphoramidite; and at least one of $R_1$, $R_2$ and $R_3$ is an O-alkyl with 16–18 carbons.

2. The compound of claim 1, wherein $R_2$ is O-phosphoramidite.

3. The compound of claim 2, wherein $R_1$ and $R_3$ are an O-alkyl with 16–18 carbons.

4. A compound having the following structure:

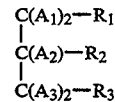

wherein $A_1$, $A_2$ and $A_3$ are selected from the group consisting of $CH_3$ and H, and $R_1$, $R_2$ and $R_3$ are selected from the group consisting of O-alkyl with 16–18 carbons an O-trityl moiety, and O-phosphoramidite;

at least one of $R_1$ and $R_3$ is O-phosphoramidite; and at least one of $R_1$, $R_2$ and $R_3$ is an O-alkyl with 16–18 carbons.

* * * * *

UNITED STATES PATENT AND TRADEMARK OFFICE
CERTIFICATE OF CORRECTION

PATENT NO. : 5,420,330
DATED : May 30, 1995
INVENTOR(S) : Charles K. Brush It is certified that error appears in the above-identified patent and that said Letters Patent is hereby corrected as shown below:

Column 5, line 55, "(0,007 mol)" should read --(0.007 mol)--.

Column 5, line 56, "(0,007 mol)" should read --(0.007 mol)--.

Column 6, line 52, "Add" should read --3. Add--.

Column 6, line 53, "Continue" should read --4. Continue--.

Column 7, line 11, "16-18 carbons an O-trityl" should read --16-18 carbons, an O-trityl--.

Column 8, line 13, "16-18 carbons an O-trityl" should read --16-18 carbons, an O-trityl--.

Signed and Sealed this

Second Day of January, 1996

*Attest:*

BRUCE LEHMAN

*Attesting Officer*     *Commissioner of Patents and Trademarks*